US00PP26284P2

(12) United States Plant Patent
Horvath

(10) Patent No.: US PP26,284 P2
(45) Date of Patent: Dec. 29, 2015

(54) ***ANDROPOGON GERARDII* PLANT NAMED 'RAIN DANCE'**

(50) Latin Name: *Andropogon gerardii*
Varietal Denomination: Rain Dance

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 137 days.

(21) Appl. No.: 13/998,073

(22) Filed: Sep. 30, 2013

(51) Int. Cl.
*A01H 5/12* (2006.01)

(52) U.S. Cl.
USPC ..... Plt./384

(58) Field of Classification Search
USPC ..... Plt./388, 384
See application file for complete search history.

*Primary Examiner* — Anne Grunberg

(57) ABSTRACT

A new, distinct *Andropogon gerardii* plant as shown and described, characterized by thinner dark green foliage below flower stems reaching a height of 140-160 cm, and maroon red fall color.

1 Drawing Sheet

Latin name: *Andropogon gerardii.*
Cultivar name: 'Rain Dance'.

BACKGROUND OF THE INVENTION

The present invention relates to a new form of *Andropogon gerardii* plant named 'Rain Dance'. 'Rain Dance' is a seedling of *Andropogon gerardii* 'Indian Warrior', U.S. Plant Pat. No. 24,999, characterized by thinner dark green foliage below flower stems reaching a height of 140-160 cm, and maroon red fall color, compared to wider green to red foliage and the taller habit of 150-180 cm of the parent plant. The new plant was sown as open pollinated seed from of *Andropogon gerardii* 'Indian Warrior', U.S. Plant Pat. No. 24,999, by the inventor at a wholesale perennial nursery in Hebron, Ill. in 2009. The seedling was grow was grown at a nursery in Hebron, Ill. The selection of this plant was due to its thinner dark green foliage below flower stems reaching a height of 140-160 cm, and maroon red fall color. Asexual, vegetative division propagation has been the only means of reproduction. Propagation has taken place at Hebron, Ill. since 2010. In 2011 we planted 60 plants in 1 gallon pots. To date these plants have remained uniform in height, and foliage color. The new *Andropogon gerardii* has shown to be stable and identical in reproduction to the parent after making over 120 vegetative divisions from 2010 to 2013.

SUMMARY OF THE INVENTION

In the following description, color references are made to The Royal Horticultural Society Colour Chart (copyright 2001). The new *Andropogon gerardii* plant named 'Rain Dance' has shown the characteristics of thinner dark green foliage below flower stems reaching a height of 140-160 cm, and maroon red fall color to be unique and stable. For purpose of the comparison the new plant will be referred to as 'Rain Dance'.

Plants of 'Rain Dance' can be compared to plants of *Andropogon gerardii* 'Indian Warrior', U.S. Plant Pat. No. 24,999. 1. 'Rain Dance' has thinner foliage and a height in the range of 140-160 cm compared to the height of *Andropogon gerardii* 'Indian Warrior' which has wider foliage and an average height of 150-180 cm. 2. 'Rain Dance' has a foliage color of 137 D coloring to N 187 A and eventually close to 200 A compared to *Andropogon gerardii* 'Indian Warrior' which has foliage color of 137 A coloring to N 77 A.

Plants of 'Rain Dance' can be also be compared to plants of *Andropogon gerardii* 'Red Bull' not patented. 1. The 'Rain Dance' has a height in the range of 140-160 cm compared to the height of *Andropogon gerardii* 'Red Bull' which has an average height of 180-210 cm. 2. 'Rain Dance' has a foliage color of 137 D coloring to N 187 A and eventually close to 200 A compared to *Andropogon gerardii* 'Red Bull' which has foliage color that is lighter green, close to 136 C. 3. 'Rain Dance' has a uniform red fall color 200 A and is propagated by division while the *Andropogon gerardii* 'Red Bull' has a variable orange red fall color and is propagated by seed.

DESCRIPTION OF PHOTOGRAPHS

Figure 1:
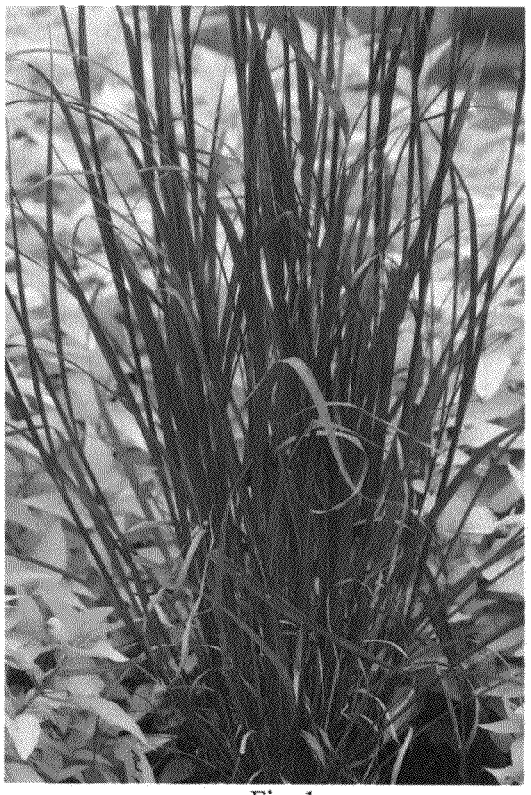
Figure 2:
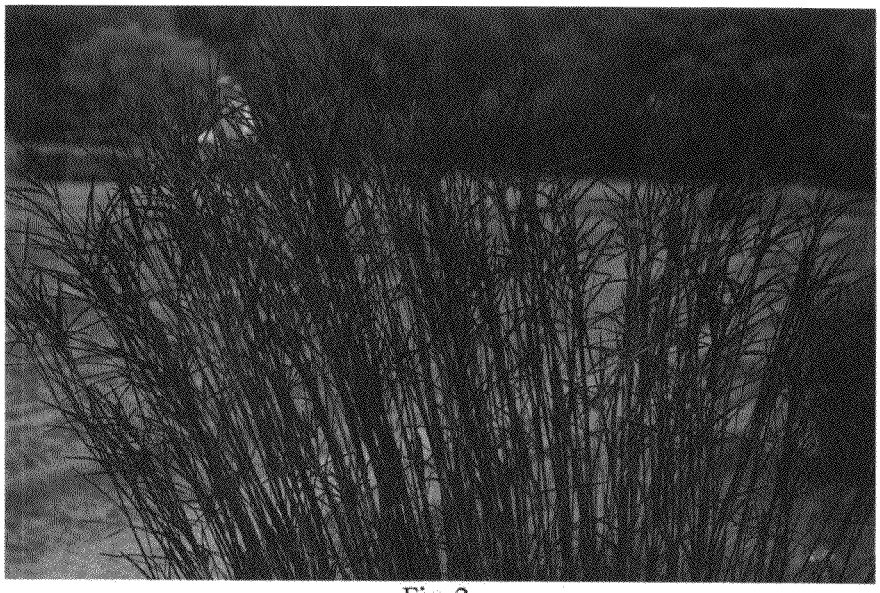

FIG. 1. Shows a potted plant with fall color in September.
FIG. 2. Shows a mature plant in bloom in August.

DETAILED BOTANICAL DESCRIPTION

In the following description, color references are made to The Royal Horticultural Society Colour Chart. The plant herein described is an established 3 year old plant growing in a garden, grown in full sun and irrigated in Hebron, Ill. USA. Measurements and numerical values represent averages of typical plants.

Botanical classification: *Andropogon gerardii* cultivar 'Rain Dance'.

Parentage: Female *Andropogon gerardii* 'Indian Warrior' U.S. Plant Pat. No. 24,999. Male parent an unknown *Andropogon gerardii.*

Propagation: Vegetative division.

Plant description: Overall habit of the new *Andropogon* is clumping with upright culms topped by red colored flowers beginning in August. Vigor is moderate.

*Plant height.*—140-160 cm.

*Plant width.*—60-80 cm.

Roots: Color — 177B, width 1-2 mm, longer than 30 cm.

Rhizomes: Width 4-5 mm, length 22 mm.

Foliage and stems:

*Foliage description*.—Glabrous, flat blade, sheathed from node of attachment to ligule, linear.

*Type*.—Deciduous, grass growing in culms.

*Shape*.—Blade.

*Sheath*.—8-9 mm wide, 16 cm long, surface — glabrous.

*Ligules*.—Up to 2 mm long and up to 6 mm wide.

*Number of blades*.—Typically 3 to 4 blades per stem.

*Blade length*.—6-7 mm wide, up to 30 cm long, ranging from 10 to 30 cm with out the sheath.

*Sheath*.—8-9 mm wide, ranging from 13 to 16 cm long.

*Adaxial leaf description*.—Leaf color is green color 137 D coloring up to N 187 A and eventually to 200 A.

*Abaxial leaf description*.—Leaf color is green color 144 B coloring up to N 187 B.

*Veins*.—Parallel, same color as surrounding leaf on both top and bottom of leaf.

*Culm description*.—Erect, cylindrical, typically with 3 or 4 leaves.

*Culm or stem diameter*.—5 mm average, but typically 3-4 mm between the nodes and swelling to 6-7 mm at the base of the internodes.

*Number of culms or stems per clump*.—Over 100.

*Node description*.—Cylindrical.

*Number of nodes per culm*.—Average 6.

*Length of internodes*.—Ranges from 13-16 cm.

Flower inflorescence:

*Inflorescence type*.—Terminal raceme with sessile and pedicillate spikelets.

*Rachis*.—1-2 mm wide and up to 55 cm long, color starts 137 D coloring up to N 187 A and eventually to 200 A.

*Overall raceme size*.—7-8 cm wide, 11 cm long.

*Rames*.—Mostly 5, 1 mm wide, 20 cm long.

*Inflorescence color*.—As a whole the color is 200 A.

*Spikelet*.—Sessile and pedicellate — both 6-10 cm long, color is 200 A.

*Rachilla*.—Less than 1 mm wide, 5 mm long, color starts 137 D coloring to 200 A.

*Individual floret size*.—1 mm wide, 15 mm long including awn.

*Lower glume*.—2 mm wide, 8 mm long, color starts 137 D coloring up to 200 A.

*Lemma*.—Outer and inner — both, 1 mm wide, 8 mm long, color starts 137 D coloring up to 200 A.

*Awn size*.—Is less than 1 mm wide and average 6 mm long.

*Pedicels*.—4 to 5 per, rames and are shorter toward the base of the plant, 1 mm wide and 5-9 cm long.

*Flower number*.—Approximately 18 florets per rames, average 54 per spikelet, mature spikelet measuring 5 cm wide, 10 cm long.

Gynoecium: Stigma — 2. color close to 200 A.

Androecium: Anthers — number 3, color — is orange.

*Anther size*.—2-4 mm long by 1 mm wide.

*Fertility*.—Fertile with 3 Anthers and 3 Stamens.

*Blooming habit*.—Terminal raceme on up to 140-160 cm stems.

*Bloom period and duration*.—Last two weeks of August to the end of September.

*Bloom color*.—200 A.

*Fruit or seeds*.—Color is 200 A, size is 2 mm wide, 11 mm long.

*Scent*.—No scent.

*Roots*.—Stiff, fibrous, and freely branching.

*Fruit*.—Seed identical to the species except color is more red, 200 A.

Hardiness: United States Department of Agriculture Zones 4-9.

Disease resistance: Plants are not susceptible to any major pests or diseases.

I claim:

1. A new, distinct *Andropogon gerardii* plant as illustrated and described, characterized by a more upright plant with a height of 140-160 cm, dark green colored foliage with red tips most of the growing season, and burgundy red fall color that turns scarlet.

* * * * *